US00PP33854P2

(12) United States Plant Patent
Blom

(10) Patent No.: US PP33,854 P2
(45) Date of Patent: Jan. 11, 2022

(54) ***CHRYSANTHEMUM* PLANT NAMED 'ZANMUHAL'**

(50) Latin Name: ***Chrysanthemum* X *morifolium***
Varietal Denomination: Zanmuhal

(71) Applicant: Wilhelmus Bernardus Blom, Leimuiden (NL)

(72) Inventor: Wilhelmus Bernardus Blom, Leimuiden (NL)

(73) Assignee: VAN ZANTEN BREEDING B.V., Rijsenhout (NL)

( * ) Notice: Subject to any disclaimer, the term of this patent is extended or adjusted under 35 U.S.C. 154(b) by 0 days.

(21) Appl. No.: 17/180,773

(22) Filed: Feb. 20, 2021

(51) Int. Cl.
*A01H 5/02* (2018.01)
*A01H 6/14* (2018.01)

(52) U.S. Cl.
USPC ..... Plt./290

(58) Field of Classification Search
USPC ..... Plt./290, 289
CPC ... A01H 5/02; A01H 5/00; A01H 6/14; A01H 6/1424; A01H 1/107; A01H 1/121; A01H 1/1215
See application file for complete search history.

(56) References Cited

U.S. PATENT DOCUMENTS

PP29,449 P2 * 7/2018 Jacobs ..... Plt./296

* cited by examiner

*Primary Examiner* — June Hwu
(74) *Attorney, Agent, or Firm* — C. Anne Whealy

(57) ABSTRACT

A new and distinct cultivar of *Chrysanthemum* plant named 'Zanmuhal', characterized by its upright, outwardly spreading and uniformly spherical plant habit; vigorous growth habit; freely branching habit, dense and full plant habit; dark green-colored leaves; uniform and freely flowering habit; long flowering period; decorative-type inflorescences with ray florets that are orange yellow in color; and good garden performance.

1 Drawing Sheet

Botanical designation: *Chrysanthemum* X *morifolium*.
Cultivar denomination: 'ZANMUHAL'.

BACKGROUND OF THE INVENTION

The present invention relates to a new and distinct cultivar of *Chrysanthemum* plant, botanically known as *Chrysanthemum* X *morifolium*, commercially referred to as a Garden Mum and hereinafter referred to by the name 'Zanmuhal'.

The new *Chrysanthemum* plant is a product of a planned breeding program conducted by the Inventor in Rijsenhout, The Netherlands. The objective of the breeding program is to create new uniform spherically-shaped and freely flowering *Chrysanthemum* plants with unique and attractive ray floret coloration.

The new *Chrysanthemum* plant originated from a cross-pollination in October, 2013 of a proprietary selection of *Chrysanthemum* x *morifolium* identified as code number 22.2339, not patented, as the female, or seed, parent with a proprietary selection of *Chrysanthemum* x *morifolium* identified as code number 10-010408, not patented, as the male, or pollen, parent. The new *Chrysanthemum* plant was discovered and selected as a single flowering plant from within the progeny of the stated cross-pollination in a controlled greenhouse environment in Rijsenhout, The Netherlands in October, 2014.

Asexual reproduction of the new *Chrysanthemum* plant by vegetative terminal cuttings was first conducted in a controlled greenhouse environment in Rijsenhout, The Netherlands since November, 2014. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'Zanmuhal'. These characteristics in combination distinguish 'Zanmuhal' as a new and distinct *Chrysanthemum* plant:

1. Upright, outwardly spreading and uniformly spherical plant habit; vigorous growth habit.
2. Freely branching habit; dense and full plant habit.
3. Dark green-colored leaves.
4. Uniform and freely flowering habit.
5. Long flowering period.
6. Decorative-type inflorescences with ray florets that are orange yellow in color.
7. Good garden performance.

Plants of the new *Chrysanthemum* can be compared to plants of the female selection parent. Plants of the new *Chrysanthemum* differ primarily from plants of the female parent selection in the following characteristics:

1. Under natural season conditions, plants of the new *Chrysanthemum* flower earlier than plants of the female parent selection.
2. Ray florets of plants of the new *Chrysanthemum* are orange yellow in color whereas ray florets of the female parent selection are bronze in color.

Plants of the new *Chrysanthemum* can be compared to plants of the male selection parent. Plants of the new

*Chrysanthemum* differ primarily from plants of the male parent selection in the following characteristics:

1. Under natural season conditions, plants of the new *Chrysanthemum* flower earlier than plants of the male parent selection.
2. Inflorescences of plants of the new *Chrysanthemum* do not have disc florets whereas inflorescences of plants of the male parent selection have disc florets.

Plants of the new *Chrysanthemum* can also be compared to plants of *Chrysanthemum* X *morifolium* 'Zanmucopper', disclosed in U.S. Plant Pat. No. 29,449. In side-by-side comparisons, plants of the new *Chrysanthemum* differ primarily from plants of 'Zanmucopper' in the following characteristics:

1. Under natural season conditions, plants of the new *Chrysanthemum* flower earlier than plants of 'Zanmucopper'.
2. Ray florets of plants of the new *Chrysanthemum* are orange yellow in color whereas ray florets of 'Zanmucopper' are bronze in color.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. The photograph comprises a top perspective view of a typical flowering plant of 'Zanmuhal' grown in a container.

DETAILED BOTANICAL DESCRIPTION

The aforementioned photograph and following observations and measurements describe plants grown in 17-cm containers in an outdoor nursery in Rijsenhout, The Netherlands under natural daylengths during the summer and autumn and under cultural practices generally used in commercial *Chrysanthemum* production. During the production of the plants, day temperatures ranged from 15° C. to 25° C. and night temperatures ranged from 8° C. to 15° C. Plants were 15 weeks from planting when the photograph was taken and the detailed description was taken on plants from 12 to 17 weeks after planting. In the following description, color references are made to The Royal Horticultural Society Colour Chart, 2015 Edition, except where general terms of ordinary dictionary significance are used.

Botanical classification: *Chrysanthemum* X *morifolium* 'Zanmuhal'.

Parentage:

*Female, or seed, parent*.—Proprietary selection of *Chrysanthemum* X *morifolium* identified as code number 22.2339, not patented.

*Male, or pollen, parent*.—Proprietary selection of *Chrysanthemum* X *morifolium* identified as code number 10-010408, not patented.

Propagation:

*Type cutting*.—By vegetative tip cuttings.

*Time to initiate roots, summer*.—About six to eight days at temperatures about 12° C. to 23° C.

*Time to produce a rooted young plant, summer*.—About 12 to 13 days at temperatures about 12° C. to 23° C.

*Root description*.—Fine, fibrous; typically close to 164D in color, actual color of the roots is dependent on substrate composition, water quality, fertilizer type and formulation, substrate temperature and physiological age of roots.

*Rooting habit*.—Freely branching; dense.

Plant description:

*Appearance*.—Perennial decorative-type *Chrysanthemum*; stems upright and outwardly spreading giving a uniformly rounded appearance to the plant; plants roughly spherical in overall shape; very freely branching habit, about nine to ten primary lateral branches develop, each primary lateral branch with about ten secondary branches; dense and full plant habit; vigorous growth habit and rapid growth rate.

*Plant height*.—About 30 cm.

*Plant width*.—About 30 cm.

*Lateral branches*.—Length: About 20 cm. Diameter: About 2 mm. Internode length: About 1 cm to 2.5 cm. Strength: Moderately strong. Aspect: About 30° to 45° from vertical. Texture and luster: Pubescent; longitudinally ridged; matte. Color: Close to 138B; with development, becoming closer to 199C.

*Leaves*.—Arrangement: Alternate, simple. Length: About 2.5 cm to 6 cm. Width: About 1 cm to 4 cm. Shape: Elliptic to obovate. Apex: Acute. Base: Obtuse to truncate. Margin: Palmately lobed, sinuses between lateral lobes divergent and relatively deep. Texture and luster, upper surface: Pubescent; slightly glossy. Texture and luster, lower surface: Pubescent; matte. Venation: Pinnate. Color: Developing and fully expanded leaves, upper surface: Close to NN137A; venation, close to 138D. Developing and fully expanded leaves, lower surface: Close to 138A; venation, close to 138C. Petioles: Length: About 1 cm. Diameter: About 2 mm. Strength: Moderately strong. Texture and luster, upper surface: Coarse, glabrous; matte. Texture and luster, lower surface: Smooth, glabrous; matte. Color, upper surface: Close to 138A. Color, lower surface: Close to 138D.

Inflorescence description:

*Appearance*.—Decorative-type inflorescence form; inflorescences borne on terminals above foliar plane; ray florets arranged acropetally on a capitulum; inflorescences facing upright to outwardly.

*Fragrance*.—Faintly fragrant, pungent.

*Flowering response*.—Under natural season conditions, plants flower from week 37 to week 42 in The Netherlands.

*Postproduction longevity*.—Inflorescences maintain good color and substance for about four weeks in an outdoor nursery; inflorescences persistent.

*Quantity of inflorescences*.—About 800 inflorescences develop per plant.

*Inflorescence buds*.—Height: About 2 mm. Diameter: About 5 mm. Shape: Rounded. Texture and luster: Smooth, glabrous; matte. Color: Close to 147D.

*Inflorescence diameter*.—About 3.5 cm.

*Inflorescence depth* (*height*).—About 1.8 cm.

*Disc diameter*.—To date, disc floret development has not been observed on plants of the new *Chrysanthemum*.

*Receptacle diameter*.—About 3 mm.

*Receptacle height*.—About 4 mm.

*Receptacle shape*.—Domed.

*Receptacle color*.—Close to 144D.

*Ray florets*.—Number of ray florets per inflorescence: About 120 to 130 ray florets arranged in about ten whorls. Length, developing: About 1 cm. Length, developed: About 2 cm. Width, developing: About 1 mm. Width, developed: About 5 mm to 6 mm. Shape, developing: Narrowly elliptic. Shape, developed: Elliptic. Apex, developing: Acute. Apex, developed: Emarginate. Base, developing and developed: Obtuse. Margin, developing and developed: Entire; slightly undulate. Aspect, developing and developed: Mostly flat. Texture and luster, developing and developed, upper and lower surfaces: Smooth, glabrous; matte. Color: When opening, upper surface: Close to 175B. When opening, lower surface: Close to 172B. Fully opened, upper surface: Close to 16B; color becoming closer to 163C development. Fully opened, lower surface: Close to 162A overlain with close to 175D; color becoming closer to 176D with development.

*Phyllaries*.—Number of phyllaries per inflorescence: About 18 phyllaries arranged in about three whorls. Length: About 2 mm to 3 mm. Width: About 1.5 mm. Shape: Narrowly elliptic. Apex: Acute. Base: Attenuate. Margin: Entire. Texture and luster, upper and lower surfaces: Pubescent; semi-glossy. Color, upper surface: Close to 138B. Color, lower surface: Close to 141B.

*Peduncles*.—Length, terminal peduncle: About 4.5 cm. Length, third peduncle: About 8 cm. Diameter, terminal and third peduncles: About 1.5 mm. Strength: Moderately strong. Texture and luster: Pubescent; matte. Color: Close to 138C.

*Reproductive organs*.—Androecium: Not observed. Gynoecium: Number of pistils per ray floret: One. Pistil length: About 2 mm. Style length: About 1.5 mm. Style color: Close to 149C. Stigma diameter: About 1 mm. Stigma shape: Forked. Stigma color: Close to 12A. Ovary color: Close to 149D.

*Seeds and fruits*.—To date, seed and fruit production have not been observed on plants of the new *Chrysanthemum*.

Garden performance: Plants of the new *Chrysanthemum* have demonstrated good garden performance and will tolerate temperatures ranging from about 4° C. to about 30° C.

It is claimed:

1. A new and distinct *Chrysanthemum* plant named 'Zanmuhal' as illustrated and described.

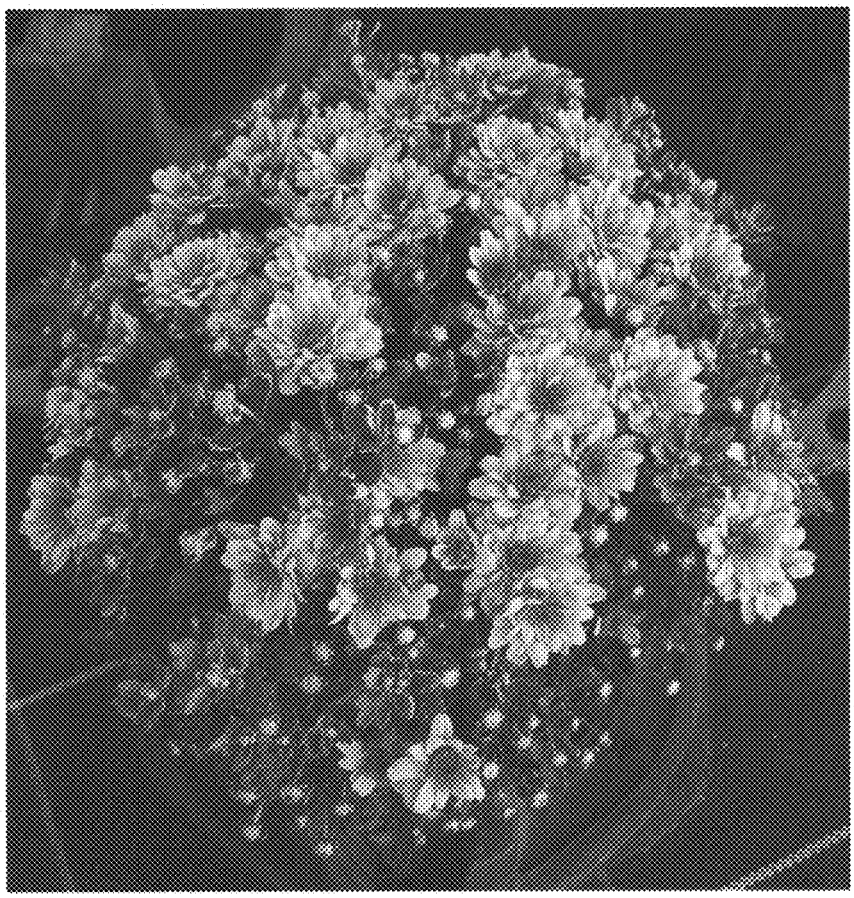

* * * * *